US012667715B2

(12) United States Patent
Tellenbach

(10) Patent No.: US 12,667,715 B2
(45) Date of Patent: Jun. 30, 2026

(54) METHOD FOR SYNCHRONIZING MULTIPLE WIRELESS EMS AND TENS DEVICES

(71) Applicant: NMES Group AB, Svenljunga (SE)

(72) Inventor: Vincent Tellenbach, Sion Valais (CH)

(73) Assignee: NMES Group AB, Svenljunga (SE)

( * ) Notice: Subject to any disclaimer, the term of this patent is extended or adjusted under 35 U.S.C. 154(b) by 231 days.

(21) Appl. No.: 18/034,870

(22) PCT Filed: Nov. 2, 2021

(86) PCT No.: PCT/EP2021/080424
§ 371 (c)(1),
(2) Date: May 1, 2023

(87) PCT Pub. No.: WO2022/090578
PCT Pub. Date: May 5, 2022

(65) Prior Publication Data
US 2024/0017056 A1     Jan. 18, 2024

Related U.S. Application Data

(60) Provisional application No. 63/198,658, filed on Nov. 2, 2020.

(51) Int. Cl.
*A61N 1/02* (2006.01)
*A61N 1/08* (2006.01)
*G16H 40/67* (2018.01)

(52) U.S. Cl.
CPC ............... *A61N 1/025* (2013.01); *A61N 1/08* (2013.01); *G16H 40/67* (2018.01)

(58) Field of Classification Search
None
See application file for complete search history.

(56) References Cited

U.S. PATENT DOCUMENTS

2012/0059436 A1* 3/2012 Fontaine .................. A61N 1/37
607/66
2018/0304074 A1 10/2018 Matsushita

FOREIGN PATENT DOCUMENTS

WO     WO 2020/190407 A1     9/2020

OTHER PUBLICATIONS

International Search Report and Written Opinion dated Feb. 16, 2022, in connection with International Application No. PCT/EP2021/080424.

* cited by examiner

*Primary Examiner* — Carl H Layno
*Assistant Examiner* — Bryan Mcallister Lee
(74) *Attorney, Agent, or Firm* — Wolf, Greenfield & Sacks, P.C.

(57) ABSTRACT

A method for synchronizing multiple wireless devices to provide electrical stimulation to muscles and nerves using Bluetooth Low Energy area network technology for the treatment of medical and non-medical conditions. This method allows Multiple Neuromuscular Electrical Stimulation (NMES) or Transcutaneous Electrical Nerve Stimulation (TENS) devices to connect and synchronize as peripherals to one central unit.

20 Claims, 8 Drawing Sheets

600

METHOD FOR SYNCHRONIZING MULTIPLE WIRELESS EMS AND TENS DEVICES

CROSS REFERENCE TO RELATED APPLICATIONS

This Application is a national stage filing under 35 U.S.C. § 371 of International Patent Application Serial No. PCT/EP2021/080424, filed on Nov. 2, 2021, entitled METHOD FOR SYNCHRONIZING MULTIPLE WIRELESS EMS AND TENS DEVICES, which claims the benefit of U.S. Provisional Application No. 63/198,658, filed on Nov. 2, 2020. The contents of these applications are incorporated herein by reference in their entirety.

FIELD OF THE INVENTION

The present invention relates, in general, to methods for synchronizing multiple wireless EMS and/or TENS devices, and systems for performing such synchronizing.

BACKGROUND

The number of medical applications that use electrical stimulation is large and covers virtually every living body component. These applications include prevention of muscle atrophy, promotion of wound healing, prevention of venous thrombosis, alleviation of both chronic/acute pain and prevention of incontinence to name but a few. Electrical stimulation may also be used for such non-medical objectives as muscle training, muscle toning, improving muscle endurance, and muscle relaxation.

Electrical stimulation of muscles and nerves is well established in medicine and physical therapy with a history dating back to mid-1850; such stimulation is currently achieved by applying electrodes to: 1) the skin at the point(s) of desired electrical stimulation; 2) through insertion of electrical probes into body cavities, and; 3) surgical insertion of electrodes; and 4) applying needles through the skin at the point(s) of desired electrical stimulation.

Neuromuscular Electrical Stimulation Principle

Muscle contractions are produced and controlled by the brain by means of electrical signals transmitted through the nervous system. When an electrical signal from the brain reaches the muscle, the latter is activated into groups of "motor units", each made up of a single neuron and of a group of associated muscle cells connected to it. This initiates a chemical reaction which causes the cells in this motor unit to contract. The complete contraction of the muscle usually involves a number of motor units simultaneously, and its strength is directly proportional to the number of activated motor units. The gradual enrolment process of the motor units which consents to a perfectly controlled and smooth muscle contraction is called spatial summation.

Electrical muscle stimulation (EMS), also known as neuromuscular electrical stimulation (NMES) or electromyostimulation, is the elicitation of muscle contraction using electric impulses. The impulses are generated by a device and are delivered through electrodes on the skin near to the muscles being stimulated. The electrodes are generally pads that adhere to the skin. The impulses mimic the action potential that comes from the central nervous system, causing the muscles to contract.

When a sufficiently intense single electrical impulse reaches the motor muscle or nerve, it causes one short single contraction of the muscle (spasm). If this single spasm is repeated and the frequency of reiteration exceeds ten spasms p.s., each following spasm is enhanced by one degree of muscle shortening caused by the preceding spasm. Such an effect is called temporal summation. The lowest stimulation frequency, where the successive contractions merge, is called tetanization frequency.

Electrical stimulation of muscles and nerves consists in the delivery of short electrical impulses. These impulses are characterized by their shape, duration, amplitude, and impulse-to-impulse duration. The effects of these different parameters and their applications are well documented in many available clinical studies.

Specific treatments may require the stimulation of different muscle groups or nerves at the same time. This can be achieved with Neuromuscular Electrical Stimulation (NMES) or Transcutaneous Electrical Nerve Stimulation (TENS) devices delivering electrical stimulation through multiple channels. Multi channels systems can present themselves as one single unit with multiple outputs. Multiple NMES or TENS can be typically used for EMS on a given body, e.g. at various different locations on the body or at various locations on a given body component.

SUMMARY

The invention is defined by the appended independent claims. Embodiments of the invention are defined in the dependent claims.

In a first aspect, there is provided a method for synchronizing electrical stimulation devices with a control device, the method comprising, at the control device: generating synchronization data; providing access to the synchronization data to a first electrical stimulation device, via a wireless communications protocol; and providing access to the synchronization data to a second electrical stimulation device, via the wireless communications protocol.

In this way, the invention provides synchronized wireless electrical stimulation. The synchronicity of the stimulation improves clinical effectiveness, for example by ensuring the stimulation program is applied effectively across the body. By way of example, a 'pulsed' stimulation program is most effective when distinct pulses of electrical current are applied to the user, with interposed periods of no electrical current. By synchronising the stimulation modules providing the stimulation program, the pulses remain distinct, and the clinical effectiveness of a pulsed stimulation program are retained.

Furthermore, the user does not notice and/or experience discomfort or confusion that may result from the application of a desynchronized stimulation program, i.e. effectively different stimulation programs being applied at different points of the body, because the stimulation devices are out of time with one another.

A wireless system is preferable to a wired system, because the removal of wires increases the ease of use, points of possible failure, and manufacturing demands of the system. Certain parts can be replaced more easily, and the modular nature of the system allows different numbers of stimulation devices to be attached for different users and/or stimulation programs.

In particular, a wireless system is advantageous if the stimulation devices are to be worn during exercise, since wires are especially disadvantageous for a user attempting to exercise.

The method may further comprise, prior to providing access to the synchronization data, at the control device: i)

scanning for devices available via the wireless communications protocol; ii) identifying the first electrical stimulation device; iii) connecting to the first electrical stimulation device; and repeating steps i) to iii) for the second electrical stimulation device.

The method may further comprise, between steps ii) and iii) for each of the first and second electrical stimulation devices, at the control device: verifying that the first or second electrical stimulation device is a device for providing electrical stimulation to a user.

The method may further comprise, prior to providing access to the synchronization data, and after step iii), at the control device: receiving first data from the first electrical stimulation device; and receiving second data from the second electrical stimulation device.

In this way, the control device is informed with the services executable by each electrical stimulation device. This may inform the stimulation patterns capable of being run, or aid in establishing a wireless connection according to certain communications protocols.

The wireless communications protocol may be Bluetooth Low Energy (BLE), the synchronization data may comprise a synchronization service and a synchronization characteristic, and the first and second electrical stimulation devices may subscribe to the synchronization characteristic.

BLE is particularly advantageous for use as a wireless communications protocol because it has a reduced power consumption relative to other protocols. This is because the BLE connection is only active for a short duration and then enters into a low power mode. The connection will stay in low power mode for a given duration and then be active again to transmit data. The duration between two active periods is called a connection interval.

The power consumption of the control and stimulation devices is therefore reduced. This may be advantageous to reduce the heat and noise generated by the device. Furthermore, if the device incorporates a portable power supply, for example a battery, the power supply may be made smaller while maintaining similar device run time and/or the run time may be increased for a certain size of power supply.

The first data may comprise at least one first service comprising at least one first characteristic, and wherein the second data comprises at least one second service comprising at least one second characteristic.

The first and second service and first and second characteristic may be the same, or may be different.

The control device may act as a central device when providing access to the synchronization data, and acts as a peripheral device when receiving the first and second data.

The method may further comprise, at the control device: updating the synchronization characteristic, wherein the first and second electrical stimulation devices are notified of the updated synchronization characteristic via subscription thereto.

In this way, the updated synchronisation characteristic is provided to each connected stimulation device within the same connection interval (i.e., within one full connection interval, each stimulation device will recognise that the synchronization characteristic has been updated). The stimulation devices can therefore be synchronized with one another by updating the synchronization characteristic.

Updating the synchronization characteristic may be initiated in response to receiving a manual input from a user at the control device. This may be advantageous if a user experiences desynchronization, or, for example, just before the user wishes to begin a stimulation session.

The method may further comprise, at the control device: measuring a latency time between the first and second electrical stimulation devices; comparing the measured latency time to a predetermined threshold; and updating the synchronization characteristic if the measured latency times exceeds the predetermined threshold. In this way, it can be ensured that desynchronization never exceeds a threshold, because the synchronization procedure is initiated automatically.

It will be appreciated that where there are more than two devices, the latency time may be a maximum latency time, i.e. the difference between the electrical devices furthest ahead in time and furthest behind in time. This can be seen most clearly in FIG. 9, depicting three devices, for example.

The method may further comprise, at the control device: initiating a stimulation program, wherein measuring a latency time between the first and second electrical stimulation devices comprises: receiving a time stamp from the first electrical stimulation device; receiving a time stamp from the second electrical stimulation device; and calculating the difference in time between the time stamps, wherein the time stamps correspond to the same predetermined point in the stimulation program.

The predetermined point in the stimulation program may, for example, be the beginning of the program, a predetermined number of impulses into the program, a predetermined cumulative amount of electrical charge delivered by the program, or any other suitable point. In essence, a point in the stimulation program is suitable if it is identifiable and independent of 'time', such that it can be used to determine the 'timing' of each stimulation program based on progress through the program.

In a second aspect, there is provided a method for synchronizing electrical stimulation devices with a control device, the method comprising, at the first electrical stimulation device: accessing synchronization data from a control device via a wireless communications protocol; and repeating steps performed by the first electrical stimulation device at the second electrical stimulation device.

The method may further comprise, at the first electrical stimulation device: advertising availability for connection via the wireless communications protocol, and wherein accessing synchronization data from the control device comprises: after identification by the control device, scanning the control device for the synchronization data; and subscribing to the synchronization data.

The method may further comprise, at the first electrical stimulation device: requesting a new connection interval from the control device; receiving the new connection interval; determining whether the new connection interval is acceptable; and completing connection if the new connection interval is acceptable or terminating connection if the new connection interval is not acceptable.

The method may further comprise, at the first electrical stimulation device: providing access to first data to the control device.

The method may further comprise, at the first electrical stimulation device: receiving instructions to implement a stimulation program; implementing the stimulation program; and sending a time stamp to the control device at one or more predetermined points during the stimulation program.

The wireless communications protocol may be Bluetooth Low Energy, the synchronization data may comprise a synchronization service and a synchronization characteristic, the first data may comprise a first service and a first characteristic, and subscription to the synchronization data may comprise implementing a notification at the first electrical stimulation device that notifies the first electrical stimulation device when the synchronization characteristic is updated at the control device.

It will be appreciated that the advantages associated with performing the method at the control device apply equally to performing the method at the stimulation devices. It will also be appreciated that any subject-matter described in relation to performing the method at either device, or both as in the third aspect, is applicable to any other method in accordance with an embodiment of the invention. In other words, if it is described that the control device provides access to synchronization data to stimulation devices, it is also described that the stimulation devices can acquire said data. Similarly, reception of data at a device is intended to be description of transmission of that data by the transmitting device, and vice versa. These examples are not limiting, and further such reversals of language will be apparent to a person skilled in the art.

In a third aspect, there is provided a method for synchronizing electrical stimulation devices with a control device using Bluetooth Low Energy, the method comprising: in a first stage, operating the control device as a central device and operating first and second electrical stimulation devices as peripheral devices, the first stage comprising: identifying, by the control device, the first and second electrical stimulation devices; connecting the control device to each of the first and second electrical stimulation devices; and transmitting a first and a second service and characteristic from the first and second electrical stimulation devices to the control device; and in a second stage, operating the control device as a peripheral device and operating the first and second electrical stimulation devices as central devices, the second stage comprising: identifying, by the first and second electrical stimulation devices, a synchronization characteristic at the control device; and subscribing, at the first and second electrical stimulation devices, to the synchronization characteristic.

The method may further comprise: initiating, by the control device, a stimulation program at the first and second electrical stimulation devices, wherein the stimulation program is implemented by the first and second electrical stimulation devices in a synchronized manner using the synchronization data, optionally wherein there is less than 50 milliseconds difference between the stimulation program at the first and second electrical stimulation devices.

In a fourth aspect, there is provided a control device configured to perform the steps of the first aspect.

In a fifth aspect, there is provided a system comprising a first and a second electrical stimulation device configured to perform the steps of the second aspect.

In a sixth aspect, there is provided a system, comprising: a control device according to the fourth aspect; and a system according to the fifth aspect.

In a seventh aspect, there is provide a system, comprising: a control device; a first electrical stimulation device; and a second electrical stimulation device, wherein the system is configured to perform the method steps of the third aspect.

The methods described above may be computer-implemented methods. In other words, the methods may be performed on processing units contained within the relevant device, for example, a processing unit on the control device and a processing unit on each of the electrical stimulation devices.

Aspects of the invention include a computer program comprising instructions which, when the program is executed by a computer, cause the computer to carry out the method of any of the first to third aspects. Aspects of the invention also include a computer-readable storage medium having stored thereon the aforementioned computer program.

The electrical stimulation devices may comprise electrodes, optionally in the form of patches or pads, for application to a user. One example of such an electrode patch is a hydrogel electrode patch.

Although throughout this specification, specific numbers of electrical stimulation devices are described, it will be appreciated that any number of electrical stimulation devices may be connected to a control device and synchronized with the control device, and with one another, according to embodiments of the invention.

The method described in the present invention enables the synchronized delivery of electrical stimulation by multiples wireless stimulation modules. The method described in the present invention enables the manual or automated synchronization of multiple wireless electrical stimulation modules by a central unit using the Bluetooth Low Energy area network technology. As a preferred embodiment, the present invention may be used to treat or improve any muscular or neural condition that is alleviated through use of electrical stimulation. It is the object of the present invention to provide a method for synchronizing multiple wireless devices to produce safe and effective transmission of electrical stimulation from the simulation device to the stimulation delivery medium, whether a hydrogel electrode, a conductive garment or a conductive accessory. It is the object of the present invention to provide a method allowing the synchronization of multiple wireless electrical stimulation devices using the Bluetooth Low Energy (BLE) area network technology. It is the object of the present invention to provide a method allowing the synchronization of multiple wireless electrical stimulation devices acting as both BLE central and peripheral devices at the same time. It is the object of the present invention to provide a method allowing the user to manually synchronize multiple wireless electrical stimulation devices. It is the object of the present invention to provide a method for automated synchronization of multiple wireless electrical stimulation devices. A primary object of the present invention is to provide electric stimulation delivery that overcomes shortcomings in prior art devices. A secondary object of the present invention is to provide an electric stimulation device, that delivers synchronized electrical impulses that trigger strong, effective muscle contractions or nerve responses in different muscle groups. Another object of the present invention is to provide an electric stimulation device that may be safely operated by medical and non-medical users. A further object of the present invention is to provide electric stimulation that is simple and safe to use. A still further object of the present invention is to provide electric stimulation that is cost and size effective for both professionals and users.

The foregoing and other objects and advantages will appear from the descriptions that follow. In the description reference is made to the accompanying drawings, which forms a part hereof, and in which is shown by way of illustration specific principles of the control method in which the invention may be practiced. These principles will be described in sufficient detail to enable those skilled in the art to practice the invention, and it is to be understood that other principles may be utilized and that structural changes may be made without departing from the scope of the invention, for example, modifications in algorithms.

BRIEF DESCRIPTION OF THE DRAWINGS

The present invention may be more completely understood when considered in conjunction with the attached drawings, in which like reference characters designate the same or similar components throughout the several views, and in which.

DETAILED DESCRIPTION

Figure 1:
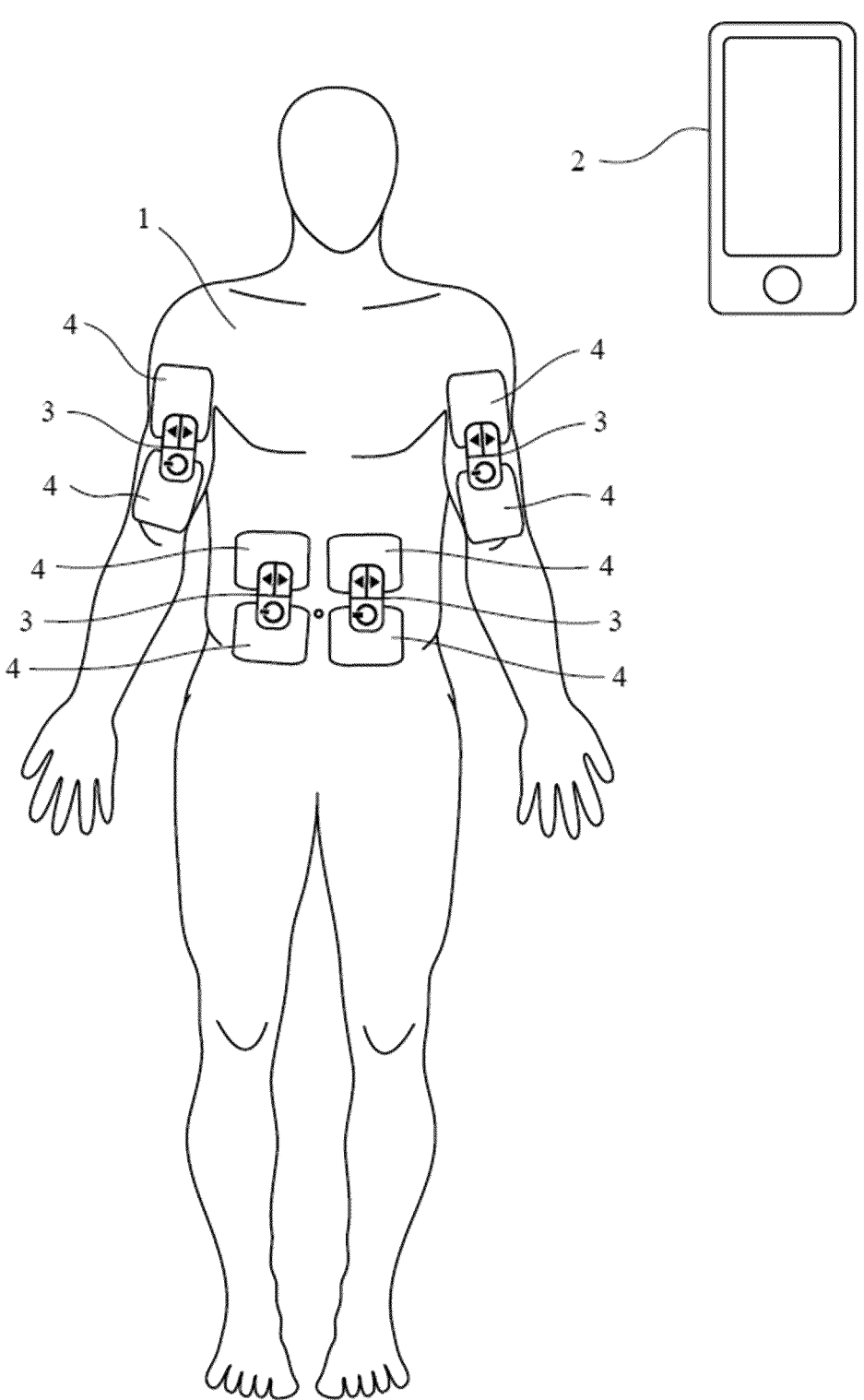
FIG. 1 depicts a system for providing synchronized electrical stimulation to a user in accordance with an embodiment of the invention.

FIG. 1 shows a possible embodiment of the present invention where several EMS and TENS devices (3) are attached to an individual (1) by the means of hydrogel electrodes (4). The EMS and TENS devices are wirelessly connected to a mobile phone (2) running a dedicated mobile application controlling the devices. The mobile application can synchronize the EMS and TENS devices by either letting the individual manually trigger the synchronization procedure or automatically starting the synchronization procedure when the latency time between the different EMS and TENS devices exceeds a given threshold value.

Figure 2:
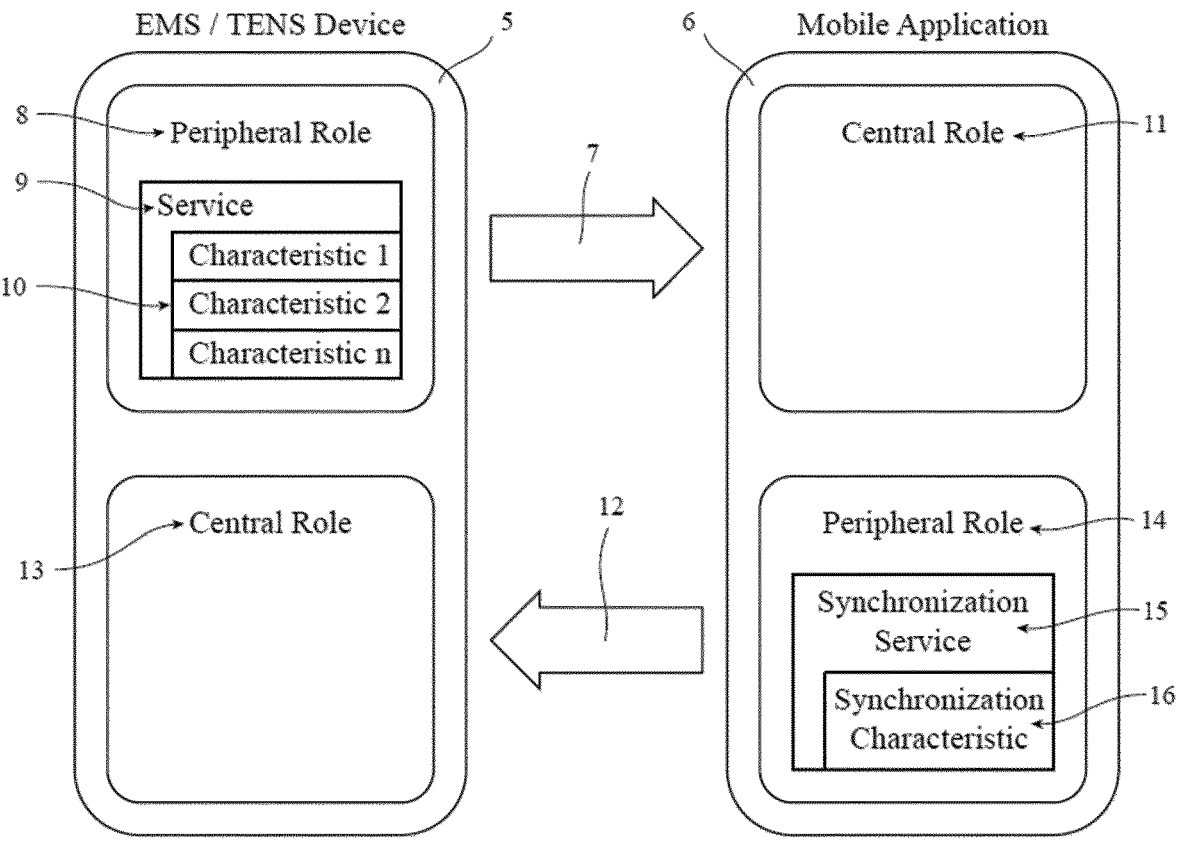
FIG. 2 depicts data transmission between a mobile application and an EMS/TENS device as a method of synchronization according to an embodiment of the invention.

FIG. 2 shows the Bluetooth Low Energy (BLE) configuration for the EMS and TENS devices (5) and the mobile application (6). A first BLE relation (7) is established where the EMS/TENS device promotes itself as a peripheral device (8) offering one or several services (9) each containing one or several characteristics (10) and the mobile application acts as a central device (11). These services and characteristics are specific for each EMS/TENS device. A second BLE relation (12) is then established where the mobile application acts as a peripheral device (14) and proposes a service (15) containing a characteristic (16) for synchronization purpose. The EMS/TENS device subscribes to that characteristic as a central device (13). All connected EMS/TENS devices subscribe to the same characteristic provided by the mobile application allowing the mobile application to send data to all EMS/TENS devices within a single instruction.

BLE

The Generic Access Profile (GAP) controls connections and advertising in Bluetooth. GAP defines various roles for devices. The following two roles will be referred to in this specification:

1. Central: the central (or master or client) device is the device that will handle the BLE communication. It will first scan for peripheral devices and connect to them.

Then it will subscribe to the peripheral device service(s) and characteristic(s) to exchange data.

Often a device with more significant processing power and configured to control the peripheral devices. May be referred to as a control device. May be a mobile device, such as a mobile phone or tablet.

2. Peripheral: the peripheral (or slave or server) device will first advertise its availability to connect to all central devices around it. After one peripheral device is successfully connected, the peripheral device stops advertising and is no more available to connect to other central devices. The peripheral device provides service(s) and characteristic(s) to which the central device can subscribe in order to exchange data.

Often a device with less significant processing power and configured to be controlled by the central device. Wireless electrical stimulation devices and/or electrical stimulation pads with embedded transceivers and processing units may be peripheral devices, in the context of this specification.

In embodiments of the present invention, mobile devices and EMS/TENS devices can act as both central and peripheral devices, in order to exchange characteristics for both reporting characteristics sent by the peripheral device and synchronization characteristics sent by the central device.

Services and Characteristics

The Generic Attribute Profile (GATT) defines the way that two BLE devices transfer data back and forth using concepts called Services and Characteristics. GATT makes use of a generic data protocol called the Attribute Protocol (ATT), which is used to store Services, Characteristics, and related data in a lookup table using 16-bit IDs for each entry in the table.

Characteristics comprise data values which are made available to connected devices, and metadata describing the data values. A single characteristic may comprise a handle, UUID, permissions, and value. Services are groups of conceptually related characteristics, for example a group of characteristics used for a particular purpose. For example, a Heart Rate Service may comprise characteristics for a declaration attribute, a value attribute, and a configuration descriptor.

GATT is used after a dedicated connection is established between two BLE devices, i.e., the advertising process governed by GAP has already been performed.

Connections established by GAP and maintained by GATT are exclusive. In other words, a BLE peripheral can only be connected to one central device (a mobile phone, etc.) at a time. As soon as a peripheral connects to a central device, it will stop 'advertising' itself via GAP and other devices will no longer be able to see it or connect to it until the existing connection is broken.

Establishing a connection is also the only way to allow two-way communication, where the central device can send meaningful data to the peripheral and vice versa.

Sequential Instruction By the Control Device

Figure 3:
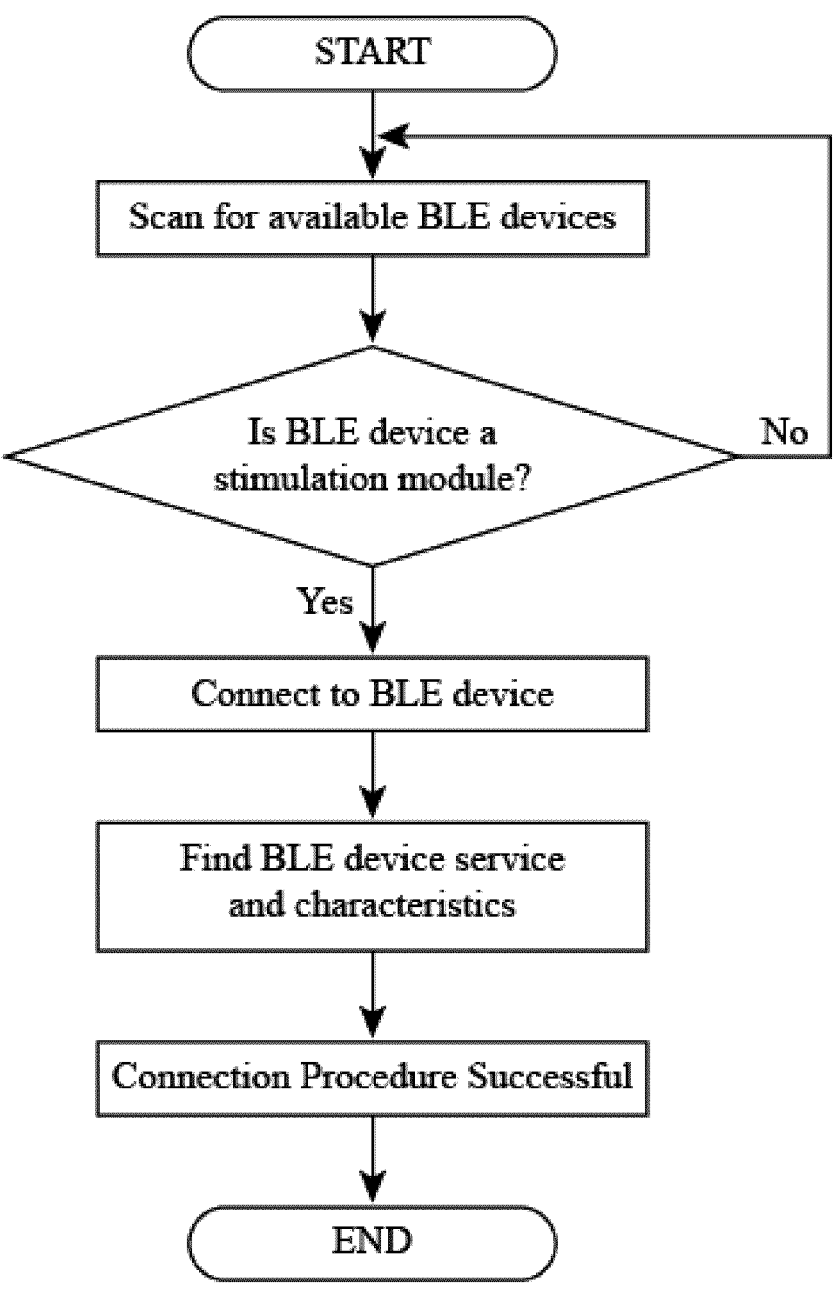
FIG. 3 depicts a connection procedure between a control and BLE device from the point of view of the control device.

FIG. 3 illustrates an exemplary connection procedure between a control device and multiple BLE devices, from the point of view of the control device. In this example, the control device acts as a central device during the method. The control device scans for available BLE devices and, once a BLE device (acting as a peripheral device) is found, the control device assesses whether the BLE device is a stimulation module (also referred to herein as an electrical stimulation device, e.g. EMS/TENS device). If the BLE device is not a stimulation module, the control device returns to scan again.

If the BLE device is an electrical stimulation device (BLE enabled), a connection is made between the control device and the an electrical stimulation device. The Electrical stimulation device transmits any stored services and characteristics to the control device.

Figure 4:
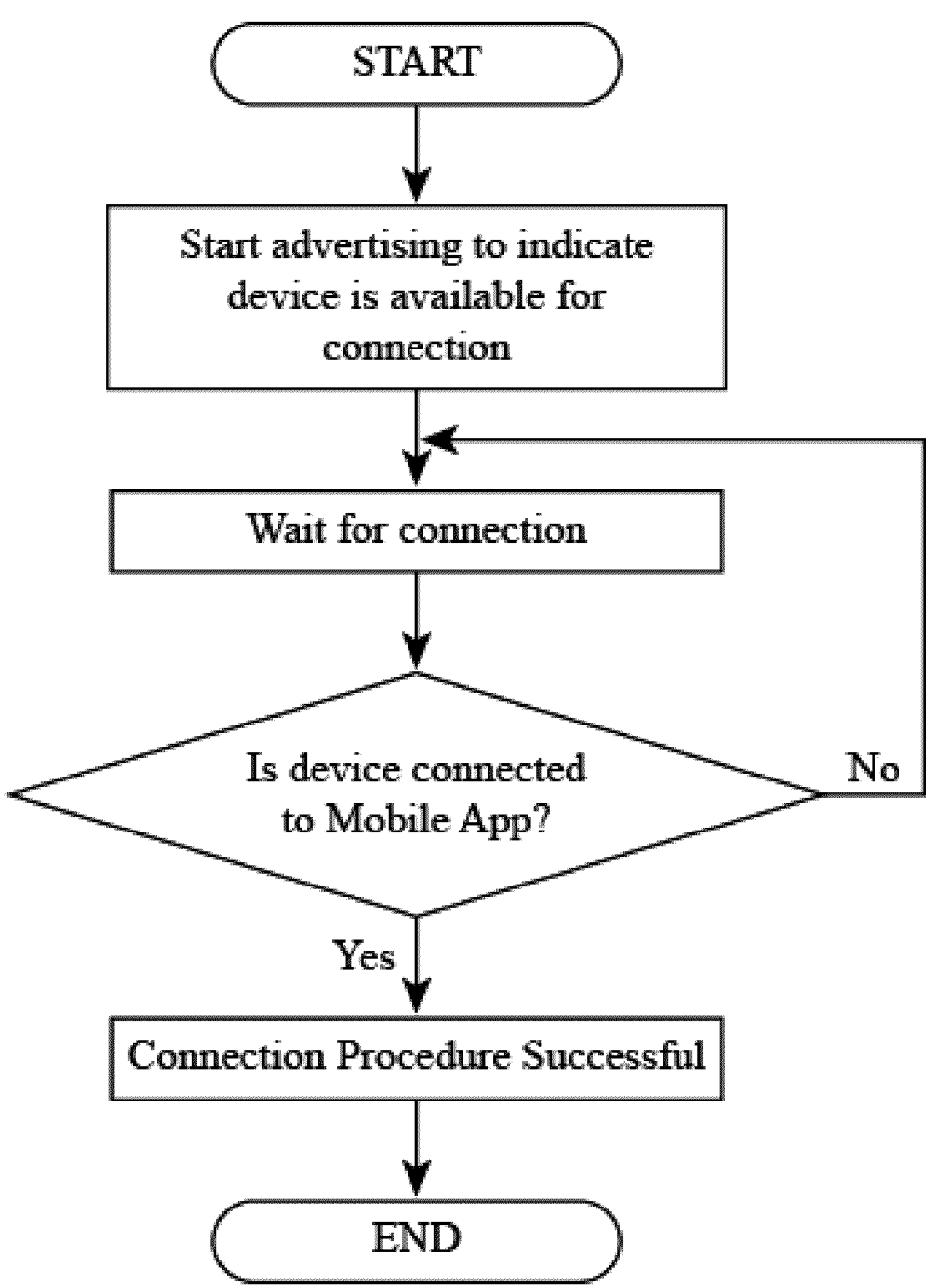
FIG. 4 depicts a connection procedure between a control and BLE device from the point of view of the BLE device.

FIG. 4 illustrates the same connection procedure illustrated in FIG. 3, but from the perspective of the electrical stimulation device. The illustrated connection procedures may be performed for a number of peripheral electrical stimulation devices, to connect each of them to the control device. In embodiments such as that shown in FIG. 1, the plurality of electrical stimulation devices are separate stimulation modules wirelessly connected to a mobile device.

In such a configuration, every connected electrical stimulation device has its own service and characteristic. When the mobile application wants to send data to all connected electrical stimulation devices, it has to do it in a sequential manner by sending the data to each connected electrical stimulation device one after the other.

Figure 5:
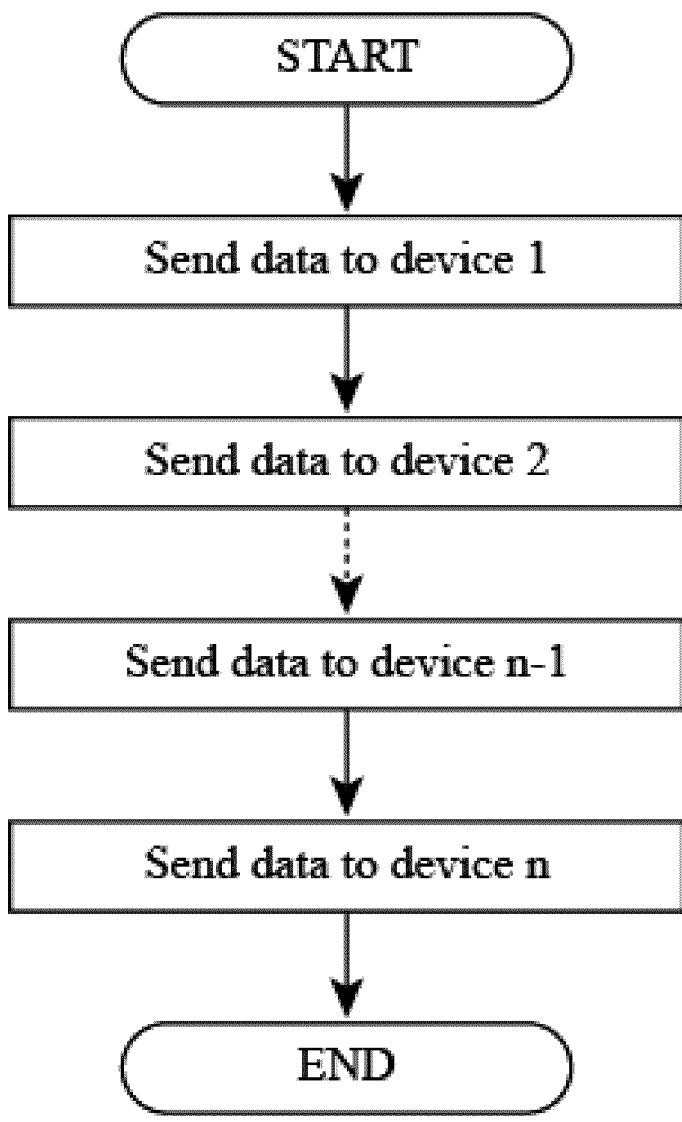
FIG. 5 depicts a sequential instructing procedure from a control device to a number of BLE devices.

FIG. 5 illustrates such a sequential instructing procedure. While the instruction data is successfully sent to each peripheral electrical stimulation device, after successful connection of each to the control device, one disadvantage is that the mobile application does not control the time interval that occurs between sending data to each device. This will depend on the mobile device operating system and the way it manages processor resources between the different applications running at the same time. This interval can vary from a few microseconds to hundreds of milliseconds. In case a user has several electrical stimulation devices connected to a mobile application, it is important that the synchronization between all the devices is kept within a time frame that will prevent the user from experiencing a delay in the electrical stimulation delivered by each device. An acceptable time frame may be considered to be below 50 milliseconds, which is an interval that will not be noticed by the vast majority of users.

Synchronized Instruction By the Control Device

Figure 6:
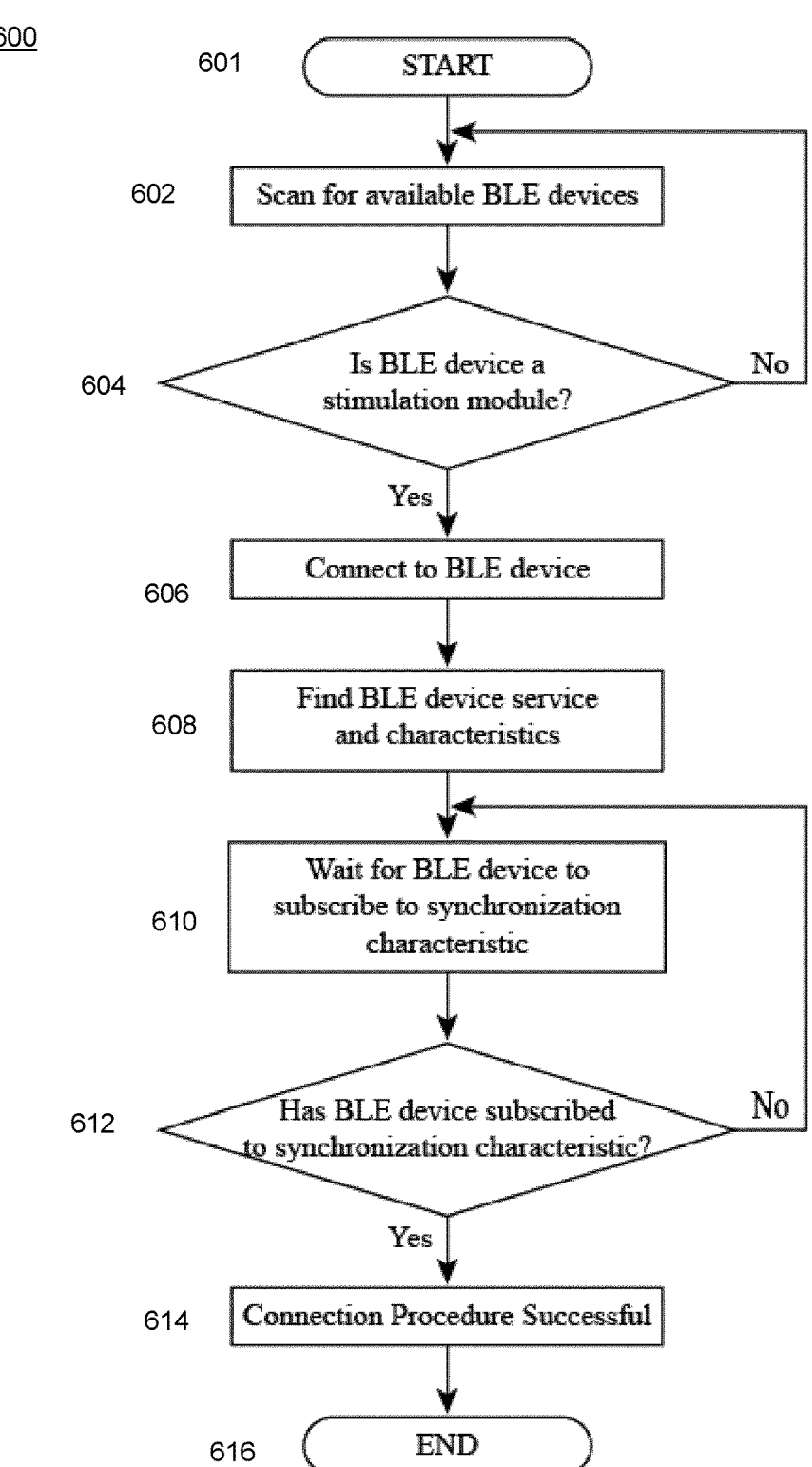
FIG. 6 depicts a connection procedure between a control and electrical stimulation device from the point of view of the control device according to an embodiment of the invention.

FIG. 6 illustrates a connection procedure 600 between a control device and a BLE device, from the point of view of the control device. The procedure begins 601 in substantially the same way as the connection procedure shown in FIG. 3. The control device scans 602 for advertising peripheral BLE devices, checks 604 whether the identified device is a stimulation module (BLE enabled), and connects 606 to it if it is. The control device then receives 608 the BLE services and characteristics. In this part of the method, the control device is acting as a central device.

In accordance with embodiments of the invention, the control device then operates as a peripheral device, offering a synchronization service and synchronization characteristic to the connected electrical stimulation device. The control device, acting as a peripheral device, may advertise itself using GAP. The electrical stimulation device, now acting as a central device, scans for the control device and connects thereto using GAP. In some embodiments, the existing connection established between the control device and the electrical stimulation device, used by the control device to receive the services and characteristics of the electrical stimulation device, can be used to avoid the scanning by the BLE device for the control device.

The control device, acting as a peripheral device, waits 610 for the connected electrical stimulation device to subscribe 612 to the synchronization characteristic.

Subscription to a characteristic, in this context, means that the connected electrical stimulation device will be updated when the control device updates the synchronization characteristic. The electrical stimulation device may enable notification in relation to the synchronization characteristic in order to achieve this. In other words, when the value defined by the synchronization characteristic changes at the control device, the connected electrical stimulation device will recognize that a change has occurred and will receive the updated value. Subscription may be considered to be achieved when the electrical stimulation device, acting as a central device, has received the synchronization service and characteristic from the control device, and has implemented a notification in relation to the synchronization characteristic.

Once the electrical stimulation device, here acting as a central device, has subscribed to the synchronization characteristic, the connection procedure is considered successful 614 and ends 616.

In embodiments of the invention, both the control device and the electrical stimulation devices act as both central and peripheral devices.

As will be appreciated, the connection procedure may be applied to a plurality of electrical stimulation devices and the single control device.

Figure 7:
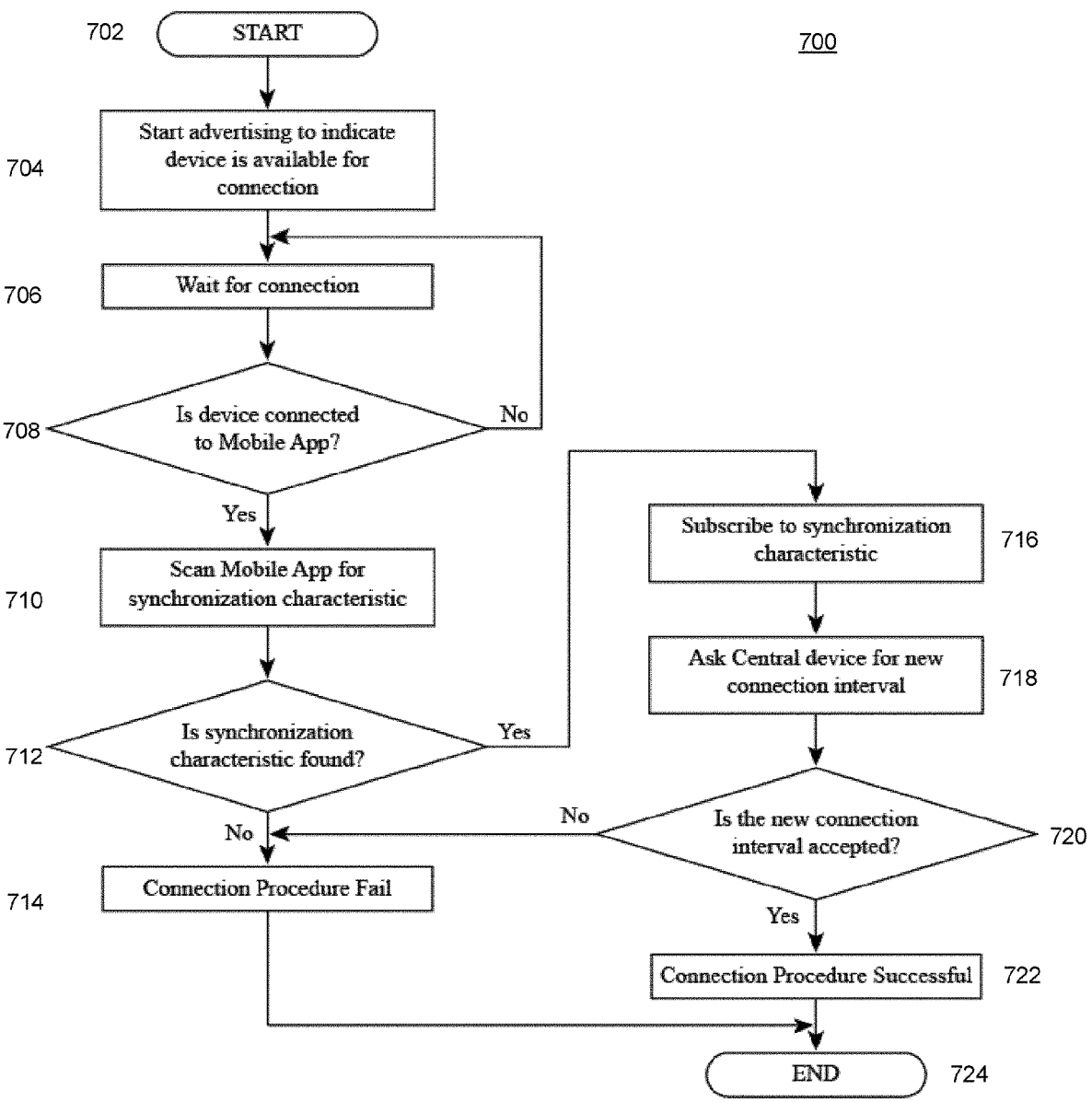
FIG. 7 depicts a connection procedure between a control and electrical stimulation device from the point of view of the electrical stimulation device according to an embodiment of the invention.

FIG. 7 illustrates the connection procedure 700, as shown in FIG. 6, between a control device and a electrical stimulation device, from the point of view of the electrical stimulation device.

The electrical stimulation device, first acting as a peripheral device, advertises 704 for connection to the control device. Once preliminary connection is achieved 706, 708, the electrical stimulation device, now acting as a control device, scans the control device (in the figure, the control device is a mobile device having a mobile application stored thereon) for a synchronization service 710 and characteristic.

If a synchronization service and characteristic are not found 714, the connection procedure is deemed to have failed and ends 724.

If a synchronization service and characteristic are found, the electrical stimulation device subscribes 716 to the synchronization characteristic as described above, including activating a notification function such that the electrical stimulation device is updated when the value of the synchronization characteristic changes.

Optionally (not shown), the connection procedure can be considered successful at this point and be terminated.

Alternatively, after the subscription to the synchronization characteristic, the electrical stimulation device, still acting as a central device, can request 718 a new connection interval from the control device. Upon receiving the new connection interval, the electrical stimulation device can either accept 720 or decline the new connection interval, leading to a successful 722 or unsuccessful connection procedure, respectively.

To ensure the BLE connection interval is below 50 milliseconds, the electrical stimulation device asks the control device to set the connection interval. One acceptable interval is less than 50 milliseconds. Another, preferred, interval is between 20 and 30 milliseconds. This request for connection interval sent by the electrical stimulation device cannot be processed by the mobile application directly, but will be processed at the operating system level of the mobile device running the mobile application.

Once connection is successful with a plurality of electrical stimulation devices, the control device can synchronize every connected electrical stimulation device with a single instruction. When the control device, for example using a mobile application, modifies the value of the synchronization characteristic, all connected electrical stimulation devices will receive the notification at the same time. The stimulation devices can then process the instruction substantially simultaneously. For example, the electrical stimulation devices can begin an electrical stimulation program substantially simultaneously, for example within 50 milliseconds of one another, preferably within 20 to 30 milliseconds of one another, such that the user perceives a simultaneous, coordinated, stimulation program.

Figure 8:
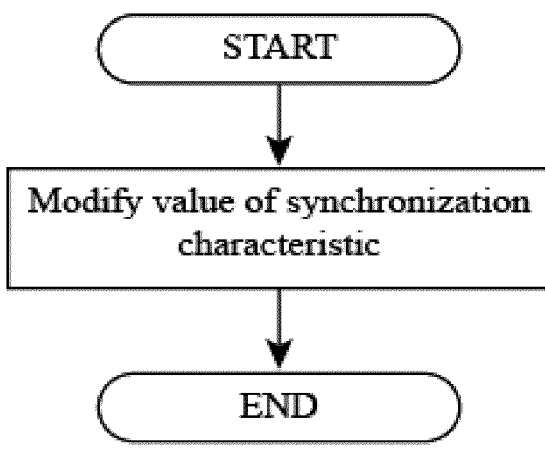
FIG. 8 depicts a process by which connected and synchronized electrical stimulation devices can be instructed by the control device.

Such a process by which all connected electrical stimulation devices can be instructed is shown in FIG. 8.

Modes of Operation—Automatic Mode

During the course of a stimulation session, the electrical stimulation devices periodically send time stamp information to the mobile application. These time stamps can be related to the elapsed duration of the stimulation program, the start of a specific pattern or cycle within the stimulation program or the number of electrical impulses generated during the stimulation program. If the delay between the reception of the time stamps from the first electrical stimulation device and the last device is greater than 50 milliseconds then the mobile application will send a synchronization command to all connected electrical stimulation devices through the synchronization characteristic. This synchronization command can ask the electrical stimulation devices to jump to a specific time in the stimulation program or to jump to a specific number of electrical impulses. All connected electrical stimulation devices will perform that synchronization command within a BLE connection interval at the latest. The synchronization between all connected electrical stimulation devices will be within 50 milliseconds. Preferably, the synchronization between all connected electrical stimulation devices will be within 20 to 30 milliseconds.

Figure 9:
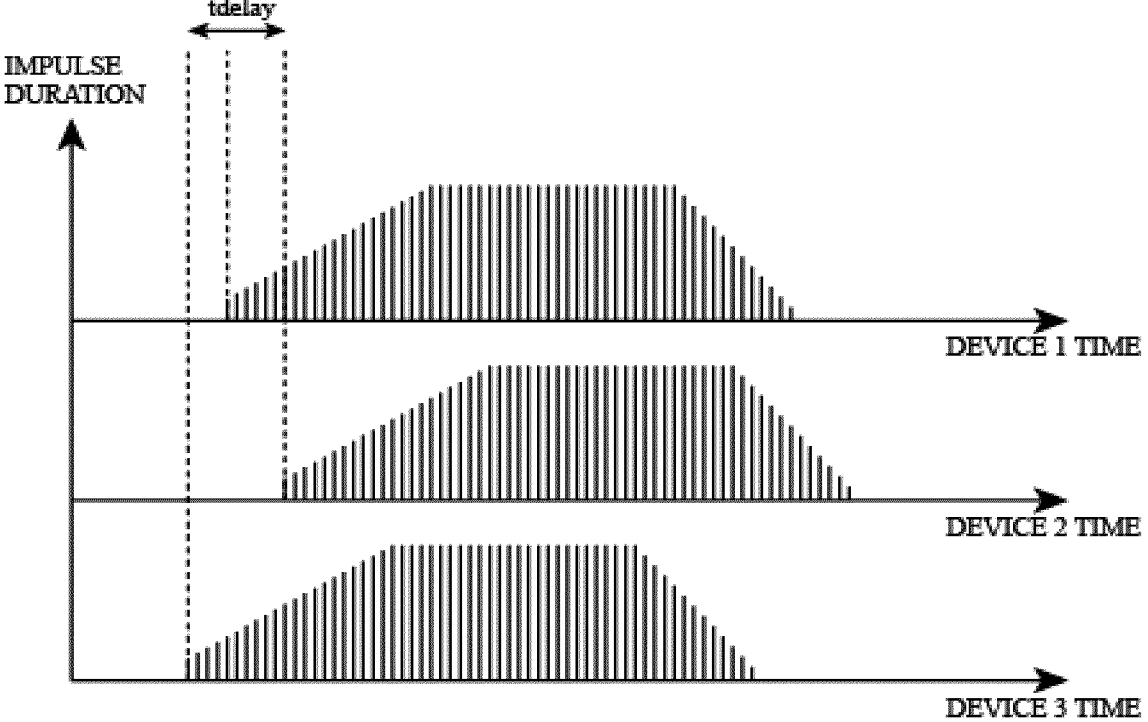
FIG. 9 depicts a graph of impulse duration against time for three devices performing a stimulation program.

FIG. 9 represents a configuration where three electrical stimulation devices are connected to the mobile application and are each performing the same stimulation program, as identified by the matching pattern in the graph of impulse duration against time. Each device sends a time stamp to the mobile application at the beginning of a pattern of the stimulation program. A value, $t_{delay}$, is calculated and represents the delay between the reception of the time stamp from the first electrical stimulation device and the time stamp from the last electrical stimulation device. The value of $t_{delay}$ is monitored, and can be adjusted, throughout the stimulation program, with further time stamps being sent by the devices at predetermined intervals in the stimulation program, as described above.

Modes of Operation—Manual Mode

The user can at any moment manually send the synchronization command described in the previous section by pressing a button on the mobile application.

Embodiments

1. A method for providing synchronized electrical stimulation to different muscle and nerve groups.

2. The method of embodiment 1 wherein the electrical stimulation is delivered to the stimulated object (individual) by the means of wireless EMS/TENS devices.

3. The method of embodiment 1 wherein the EMS/TENS devices are connected to the same controller device.

4. The method of embodiment 1 wherein the wireless protocol used to connect the EMS/TENS device to the controller device is the Bluetooth Low Energy Area Network technology.

5. The method of embodiment 1 wherein the EMS/TENS devices and the controller device both act as peripheral and central device at the same time.

Example

The electrical stimulation device may perform the following sequence:

1. Provide a BLE service for data communication with the mobile application,

2. Add a BLE characteristic to the BLE service of point 1 to notify the mobile application about any change affecting the operation of the device that is not induced by the mobile application. This characteristic should be notifiable, readable and not writable by the mobile application.

3. Add a BLE characteristic to the BLE service of point 1 to allow the mobile application to request data from the electrical stimulation device. This characteristic should be writable, not readable and not notifiable by the mobile application.

4. Add a BLE characteristic to the BLE service of point 1 to allow the electrical stimulation device to send the data value requested by the characteristic of point 3 to the mobile application. This characteristic should be notifiable, readable and not writable by the mobile application.

5. Add a BLE characteristic to the BLE service of point 1 to allow the mobile application to write data to the electrical stimulation device. This characteristic should be writable, not readable and not notifiable by the mobile application.

6. Add a BLE characteristic to the BLE service of point 1 to allow the electrical stimulation device to acknowledge the data write operation initiated by the characteristic of point 5 to the mobile application. This characteristic is also used to acknowledge the data write operation initiated by the synchronization characteristic provided by the mobile application. This characteristic should be notifiable, readable and not writable by the mobile application.

7. Start BLE advertising to inform the mobile application about the electrical stimulation device availability to connect to a Central device.

8. Once connected, scan the Central device for the synchronization characteristic.

9. Subscribe to the synchronization characteristic.

10. Ask the Central device for new connection interval.

The control device may perform the following method:

1. Provide a BLE service for synchronized data communication with all connected electrical stimulation devices.

2. Add a BLE characteristic to the BLE service of point 1 to allow the mobile application to write data simultaneously to the all connected electrical stimulation devices. This characteristic should be notifiable, readable and not writable by the electrical stimulation devices.

3. Scan for available electrical stimulation devices and connect to them.

4. Wait for the connected electrical stimulation devices to subscribe to the synchronization characteristic of point 2.

5. Start data transfer with the electrical stimulation devices.

13

The invention claimed is:

1. A method for synchronizing electrical stimulation devices with a control device, the method comprising, at the control device:

generating synchronization data;

i) scanning for devices available via a wireless communications protocol;

ii) identifying a first electrical stimulation device;

iii) connecting to the first electrical stimulation device; and repeating steps i) to iii) for a second electrical stimulation device;

providing access to the synchronization data to the first electrical stimulation device, via the wireless communications protocol;

providing access to the synchronization data to the second electrical stimulation device, via the wireless communications protocol;

receiving, from the first electrical stimulation device, a request for a first new connection interval;

receiving, from the second electrical stimulation device, a request for a second new connection interval; and sending, in response to the requests, new connection intervals to the first and second electrical stimulation devices.

2. The method according to claim 1, further comprising, between steps ii) and iii) for each of the first and second electrical stimulation devices, at the control device:

verifying that the first or second electrical stimulation device is a device for providing electrical stimulation to a user.

3. The method according to claim 1, further comprising, prior to providing access to the synchronization data, and after step iii), at the control device:

receiving first data from the first electrical stimulation device; and receiving second data from the second electrical stimulation device.

4. The method according to claim 3, wherein the first data comprises at least one first service comprising at least one first characteristic, and wherein the second data comprises at least one second service comprising at least one second characteristic.

5. The method according to claim 1, wherein the wireless communications protocol is Bluetooth Low Energy, and wherein the synchronization data comprises a synchronization service and a synchronization characteristic, and wherein the first and second electrical stimulation devices subscribe to the synchronization characteristic.

6. The method according to claim 5, wherein when the control device acts as a peripheral device when providing access to the synchronization data, and acts as a central device when receiving the first and second data.

7. The method according to claim 5, further comprising, at the control device:

updating the synchronization characteristic, wherein the first and second electrical stimulation devices are notified of the updated synchronization characteristic via subscription thereto.

8. The method according to claim 7, wherein updating the synchronization characteristic is initiated in response to receiving a manual input from a user at the control device.

9. The method according to claim 7, further comprising, at the control device:

measuring a latency time between the first and second electrical stimulation devices;

14 comparing the measured latency time to a predetermined threshold; and updating the synchronization characteristic if the measured latency times exceeds the predetermined threshold.

10. The method according to claim 9, further comprising, at the control device:

initiating a stimulation program, wherein measuring a latency time between the first and second electrical stimulation devices comprises:

receiving a time stamp from the first electrical stimulation device;

receiving a time stamp from the second electrical stimulation device; and calculating the difference in time between the time stamps, wherein the time stamps correspond to the same predetermined point in the stimulation program.

11. The method according to claim 1, further comprising:

initiating, by the control device, a stimulation program at the first and second electrical stimulation devices, wherein the stimulation program is implemented by the first and second electrical stimulation devices in a synchronized manner using the synchronization data, optionally wherein there is less than 50 milli seconds difference between execution of the stimulation program at the first and second electrical stimulation devices.

12. A control device configured to perform the steps of claim 1.

13. A method for synchronizing first and second electrical stimulation devices with a control device, the method comprising, at the first and second electrical stimulation devices:

advertising availability for connections via a wireless communications protocol;

accessing synchronization data from a control device via the wireless communications protocol, wherein accessing synchronisation data from the control device comprises:

after identification by the control device, scanning the control device for the synchronization data; and subscribing to the synchronisation data;

requesting a new connection interval from the control device;

receiving the new connection interval;

determining whether the new connection interval is acceptable; and completing connection if the new connection interval is acceptable or terminating connection if the new connection interval is not acceptable; and repeating steps performed by the first electrical stimulation device at the second electrical stimulation device.

14. The method according to claim 13, further comprising, at the first electrical stimulation device:

providing access to first data to the control device.

15. The method according to claim 13, further comprising, at the first electrical stimulation device:

receiving instructions to implement a stimulation program;

implementing the stimulation program; and sending a time stamp to the control device at one or more predetermined points during the stimulation program.

16. The method according to claim 13, wherein the wireless communications protocol is Bluetooth Low Energy, wherein the synchronization data comprises a synchronization service and a synchronization characteristic, wherein the first data comprises a first service and a first characteristic, and wherein subscription to the synchronization data comprises implementing a notification at the first electrical stimulation device that notifies the first electrical stimulation device when the synchronization characteristic is updated at the control device.

17. A system comprising a first and a second electrical stimulation device configured to perform the steps of claim 13.

18. A system, comprising:
a control device that performs the steps of:
  generating synchronization data;
    i) scanning for devices available via a wireless communications protocol;
    ii) identifying a first electrical stimulation device;
    iii) connecting to the first electrical stimulation device;
    repeating steps i) to iii) for a second electrical stimulation device
    providing access to the synchronization data to the first electrical stimulation device, via the wireless communications protocol;
    providing access to the synchronization data to a second electrical stimulation device, via the wireless communications protocol;
    receiving, from the first electrical stimulation device, a request for a new connection interval;
    receiving, from the second electrical stimulation device, a request for a new connection internal; and
    sending, in response to the requests, a new connection internal to the first and second electrical stimulation devices; and
    a system according to claim 17.

19. A method for synchronizing first and second electrical stimulation devices with a control device using a wireless communications protocol, the method comprising:
  in a first stage, operating the control device as a central device and operating first and second electrical stimulation devices as peripheral devices, the first stage comprising:

identifying, by the control device, the first and second electrical stimulation devices;
    connecting the control device to each of the first and second electrical stimulation devices; and
    transmitting a first and a second service and characteristic from the first and second electrical stimulation devices to the control device; and
  in a second stage, operating the control device as a peripheral device and operating the first and second electrical stimulation devices as central devices, the second stage comprising:
    identifying, by the first and second electrical stimulation devices, a synchronization characteristic at the control device;
  subscribing, at the first and second electrical stimulation devices, to the synchronization characteristic;
  and wherein connecting the control device to each of the first and second electrical stimulation devices comprises, at the first and second electrical stimulation devices:
    requesting a new connection interval from the control device:
    receiving the new connection interval;
    determining whether the new connection interval is acceptable; and
    completing connection if the new connection interval is acceptable or terminating connection if the new connection interval is not acceptable.

20. A system, comprising:
a control device;
a first electrical stimulation device; and
a second electrical stimulation device, wherein the system is configured to perform the method steps of claim 19.

* * * * *